(12) United States Patent
Albert (10) Patent No.: US 11,013,244 B2
(45) Date of Patent: May 25, 2021

(54) EDIBLE PET CHEW FOR DENTAL CARE OF COMPANION ANIMALS

(71) Applicant: Karen Lori Albert, Malibu, CA (US)

(72) Inventor: Karen Lori Albert, Malibu, CA (US)

( * ) Notice: Subject to any disclaimer, the term of this patent is extended or adjusted under 35 U.S.C. 154(b) by 0 days.

(21) Appl. No.: 16/409,445

(22) Filed: May 10, 2019

(65) Prior Publication Data

US 2019/0343147 A1 Nov. 14, 2019

Related U.S. Application Data

(60) Provisional application No. 62/670,327, filed on May 11, 2018.

(51) Int. Cl.

| | |
|---|---|
| *A23K 10/35* | (2016.01) |
| *A23K 50/42* | (2016.01) |
| *A23K 10/14* | (2016.01) |
| *A23K 40/30* | (2016.01) |
| *A61Q 11/00* | (2006.01) |
| *A61K 8/34* | (2006.01) |
| *A61K 8/9794* | (2017.01) |
| *A61K 8/66* | (2006.01) |
| *A61K 8/9789* | (2017.01) |

(52) U.S. Cl.
CPC .............. *A23K 10/35* (2016.05); *A23K 10/14* (2016.05); *A23K 40/30* (2016.05); *A23K 50/42* (2016.05); *A61K 8/345* (2013.01); *A61K 8/66* (2013.01); *A61K 8/9789* (2017.08); *A61K 8/9794* (2017.08); *A61Q 11/00* (2013.01)

(58) Field of Classification Search
CPC ........ A23K 10/35; A23K 50/42; A23K 10/14; A23K 40/30; A61Q 11/00; A61K 8/345; A61K 8/9794; A61K 8/66; A61K 8/9789
See application file for complete search history.

(56) References Cited

U.S. PATENT DOCUMENTS

| | | | |
|---|---|---|---|
| 5,650,184 A | 7/1997 | Humphry et al. | |
| 6,601,539 B1 * | 8/2003 | Snook | A01K 15/026 119/710 |
| 7,537,794 B2 | 5/2009 | Baldus | |
| 7,677,203 B2 * | 3/2010 | Stern | A23K 40/20 119/709 |
| 8,900,649 B1 | 12/2014 | Chen et al. | |
| 9,226,516 B2 | 1/2016 | Chen et al. | |
| 2005/0260306 A1 | 11/2005 | Baldus | |
| 2007/0289552 A1 | 12/2007 | Axelrod et al. | |
| 2009/0022673 A1 | 1/2009 | Albert | |
| 2014/0255553 A1 | 9/2014 | Xu | |
| 2015/0201656 A1 | 7/2015 | Liang et al. | |
| 2015/0282505 A1 | 10/2015 | Ziglin | |
| 2016/0158147 A1 | 6/2016 | Singer | |

* cited by examiner

*Primary Examiner* — Shirley V Gembeh
(74) *Attorney, Agent, or Firm* — Morriss O'Bryant Compagni Cannon, PLLC (57) ABSTRACT

Edible pet chews are made of one or two layers, each layer comprising a thin slice of sweet potato, and one of the layers being processed to form irregularities, the layers being rolled into a tubular body and treated with heat to form a single- or dual-layered dehydrated tube having the irregularities oriented toward the interior cavity of the tubular body, the interior cavity being fillable with a beneficial material of suitable viscosity to provide a beneficial or therapeutic effect to the animal as the animal chews on the edible pet chew.

18 Claims, 5 Drawing Sheets

EDIBLE PET CHEW FOR DENTAL CARE OF COMPANION ANIMALS

CROSS-REFERENCE TO RELATED APPLICATIONS

This is a non-provisional application that claims priority to U.S. provisional application Ser. No. 62/670,327, filed May 11, 2018, the contents of which are incorporated herein in their entirety.

TECHNICAL FIELD

This invention relates to healthcare products for animals, including companion animals, or pets, and specifically relates to edible chews made of a dual layering of dehydrated vegetable material for removing tartar from an animal's teeth, and a dehydrated structure containing a viscous fluid formulated for reducing plaque on an animal's teeth.

BACKGROUND OF THE DISCLOSURE

Chew toys are widely known and manufactured for the purpose of providing a chewable device that will clean an animal's teeth. That is, the animal finds the biting and chewing of the device a pleasurable activity, while the device scrapes the animal's teeth to provide a cleaning action. Many such chew devices are made of hardened rawhide. Other chew devices are made of combinations of animal-based materials, such as rawhide, and plastic. Other chew devices are substantially made of man-made synthetic materials. These chew devices are purposely made of hardened material that the animal can chew on for an extended period of time. However, such chew devices often chip or break the animal's teeth.

Chew devices made of animal-based materials and/or synthetic materials are intended for consumption by the animal. It is presumed that the animal will chew the device into small enough pieces that the pieces may be swallowed. However, many chew devices are not made of material that naturally breaks into small enough pieces to be swallowed. Rather, many chew devices are hard or rubbery and the animals attempts to swallow the entire chew device because it does not naturally break into small pieces. As a result, severe intestinal damage can occur if the pieces that are swallowed are too large to pass naturally or to degrade. Additionally, the undigested pieces of the pet chews can present a choking hazard, both in the animal's throat and in the digestive system. Such chew devices have also proven to contain materials that are toxic to the animal or cause allergic reactions.

Other chew toys or devices have been made of vegetable-based materials. Some vegetable-based chew devices are made of a single type of plant material, while others are made of two or more plant materials in an admixture. Some vegetable-based chew devices are formulated for providing extended, chewing by the animal, but are not necessarily constructed or devised for being edible in their entirety. Many manufactured vegetable-based chews also contain additional artificial ingredients and preservatives, gluten, wheat, added sugars, fats and other agents that are intended to provide additional nutrition to the animal and/or are intended to increase the shelf life of the chew. Many of the added agents have proven to be toxic, spoiled or otherwise deleterious to the animal's health, and also add undesirable calories to the animal's daily nutritional intake. There has been a recent correlation between consumption of chew treats by dogs and a growing obesity problem.

SUMMARY

In a first aspect, embodiments are disclosed of an edible pet chew that comprises an outer layer made of at least one slice of sweet potato and an inner layer of sweet potato positioned adjacent the outer layer of sweet potato, the inner layer having a surface oriented away from the outer layer that is formed with irregularities, wherein the outer layer and inner layer are formed together as a tubular body that is dehydrated.

In some embodiments, the outer layer further comprises a single layer of sweet potato taken from a whole potato and has a thickness that is generally one-sixteenth of an inch.

In certain embodiments, the inner layer is formed from a slice of sweet potato having a thickness at an outer edge of the slice of sweet potato that is generally one-sixteenth of an inch.

In yet other embodiments, the irregularities of the surface of the inner layer include perforations through the thickness of the inner layer.

In still other embodiments, the irregularities of the surface of the inner layer include ridge formations that extend along the length of the inner layer, along the width of the inner layer, along the bias of the inner layer or both along the length and width of the inner layer.

In certain embodiments, the tubular body has at least one open end providing access to the interior of the tubular body.

In some embodiments, the dehydrated tubular body has a moisture content of 10% or less.

In yet other embodiments, the pet chew further comprises a plaque-reducing material positioned in an interior of the tubular body.

In certain embodiments, the plaque-reducing material is a viscous material containing natural plant extracts providing surfactant-based plaque-reducing agents.

In a second aspect of the disclosure, a pet chew is formed from a single slice of sweet potato which is provided with a first side that is relatively smooth or untextured and a second side that is formed with irregularities, the second side being oriented to define an inner surface of the pet chew when the single slice of sweet potato is formed into a tubular body.

In a third aspect of the disclosure, an edible pet chew kit includes a dehydrated tubular body comprising an outer layer formed from a slice of whole sweet potato and an inner layer formed from a slice of whole sweet potato, the inner slice having surface irregularities oriented toward the center cavity of the tubular body, and the kit further includes a quantum of thickened material contained in a separate packaging unit, the quantum of thickened material being formulated for delivery into the center cavity of the tubular body.

In some embodiments, the thickened material is formulated to deliver plaque-reducing agents to the teeth of an animal.

In a fourth aspect of the disclosure, a plaque-reducing material for use in a pet chew comprises, in combination, water, sorbitol, glycerin, and natural plant extracts providing surfactant agents, the material being formulated as a viscous gel.

In some embodiments, the natural plant extracts include cinnamon extract, clove extract and yucca extract.

In certain other embodiments, the plaque-reducing material further comprises an enzyme.

In a fifth aspect, a method of making a pet chew comprises providing a first slice of sweet potato taken from a whole sweet potato, providing a second slice of sweet potato taken from a whole sweet potato, treating the second slice of sweet potato to form irregularities on at least one side of the second slice of sweet potato, positioning the second slice of sweet potato adjacent to the first slice of sweet potato to orient the at least one surface of irregularities away from the first slice of sweet potato, placing the two adjacently positioned slices of sweet potato about a mandrel, with the second slice of sweet potato positioned closest to the mandrel and with the side having irregularities positioned adjacent to the mandrel, to form a tubular body made of the first slice and second slice, exposing the tubular body to a temperature of between 150° F. and 190° F. for a period of between nine hours and twelve hours, and allowing the tubular body to cool for an additional one to three hours.

In some embodiments, the tubular body is exposed to elevated temperature while remaining positioned about the mandrel and is cooled for a period of between one and three hours while positioned about the mandrel, then followed by removal of the mandrel from the tubular body.

In certain other embodiments, a free end of the tubular body, resulting from the positioning of the first slice and second slice about the mandrel, is secured in place to maintain the tubular body in place about the mandrel prior to and during processing at an elevated temperature.

In yet other embodiments, the free end of the tubular body is secured in position by placement of comestible adhesive between the free end and the outer surface of the first slice of sweet potato.

In some other embodiments, the free end of the tubular body is secured in place by wrapping a mechanical device about the circumference of the tubular body, the mechanical device being removed after the tubular body is treated with heat.

In yet other embodiments, the first slice of sweet potato is formed with a thickness dimension of generally one sixteenth of an inch, and wherein the second slice of sweet potato is formed with a thickness dimension of generally one sixteenth of an inch.

In some embodiments, the tubular body, following the heating and cooling steps, has a moisture content of between two percent and ten percent.

In certain other embodiments, one side of the first slice of sweet potato is formed with irregularities, which side is positioned about the mandrel to be oriented away from the mandrel and away from the second slice of sweet potato.

In a sixth aspect, a method of making an edible pet chew comprises providing a first slice of sweet potato, providing a second slice of sweet potato and treating at least one side of the second slice of sweet potato to form irregularities on at least one side of the second slice of sweet potato, positioning the second slice of sweet potato adjacent to the first slice of sweet potato to orient the at least one side of irregularities away from the first slice of sweet potato, placing the two adjacently positioned slices of sweet potato about a mandrel, with the second slice of sweet potato positioned closest to the mandrel and with the side having irregularities positioned adjacent to the mandrel to form a tubular body of two layers of sweet potato, exposing the tubular body to heat to dehydrate the tubular body, and cooling the tubular body to form a dehydrated tubular body having a moisture content of between two percent and ten percent.

In some embodiments, the method further comprises inserting into the interior or central cavity of the tubular body a material having therapeutic, nutritional and/or beneficial agents for the health of an animal.

Other aspects, features, and advantages will become apparent from the following detailed description when taken in conjunction with the accompanying drawings, which are a part of this disclosure and which illustrate, by way of example, principles of the inventions disclosed.

DESCRIPTION OF THE FIGURES

The accompanying drawings facilitate an understanding of the various embodiments.

DETAILED DESCRIPTION

Figure 6:
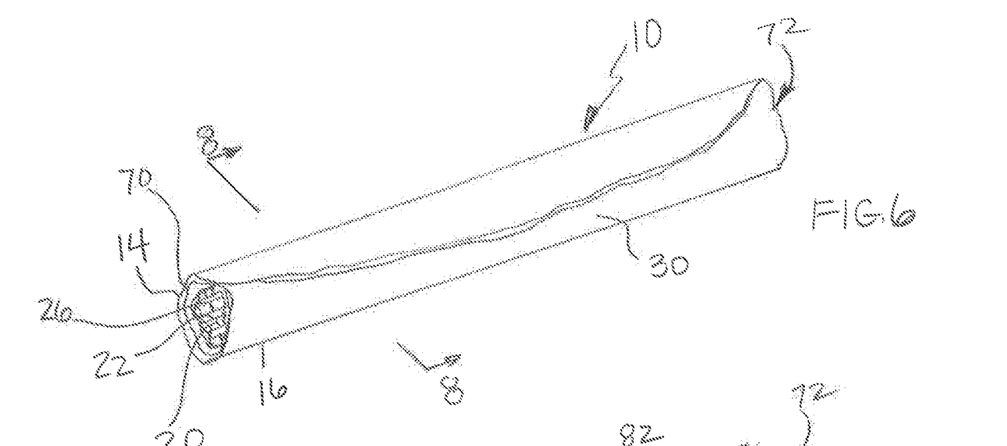
FIG. 6 is a perspective view of the tubular body in accordance with the disclosure with the mandrel removed.
Figure 7:
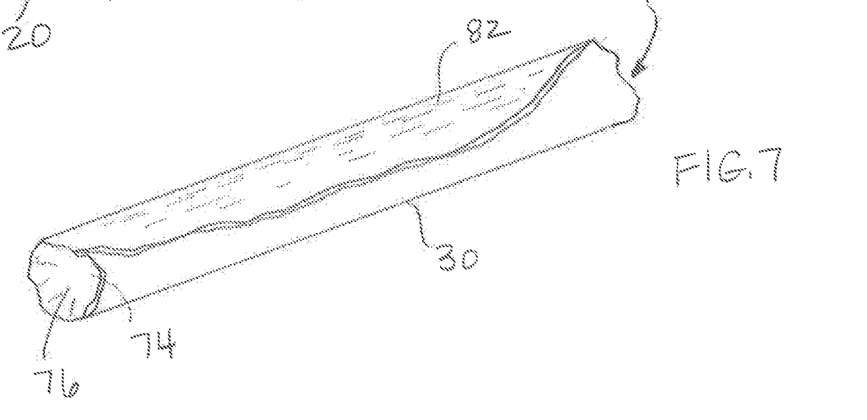
FIG. 7 is a perspective view of an alternative embodiment of the tubular body having one closed end.

As shown particularly in FIGS. 6 and 7, in accordance with a first aspect of the disclosure, an edible pet chew 10 comprises an outer layer 14 made of at least one slice 16 of sweet potato and an inner layer 20 of sweet potato positioned adjacent the outer layer 14 of sweet potato, the inner layer 20 having a surface 22 oriented away from the outer layer 14 that is formed with irregularities 26, wherein the outer layer 14 and inner layer 20 are formed together as a tubular body 30 that is dehydrated.

Figure 1:
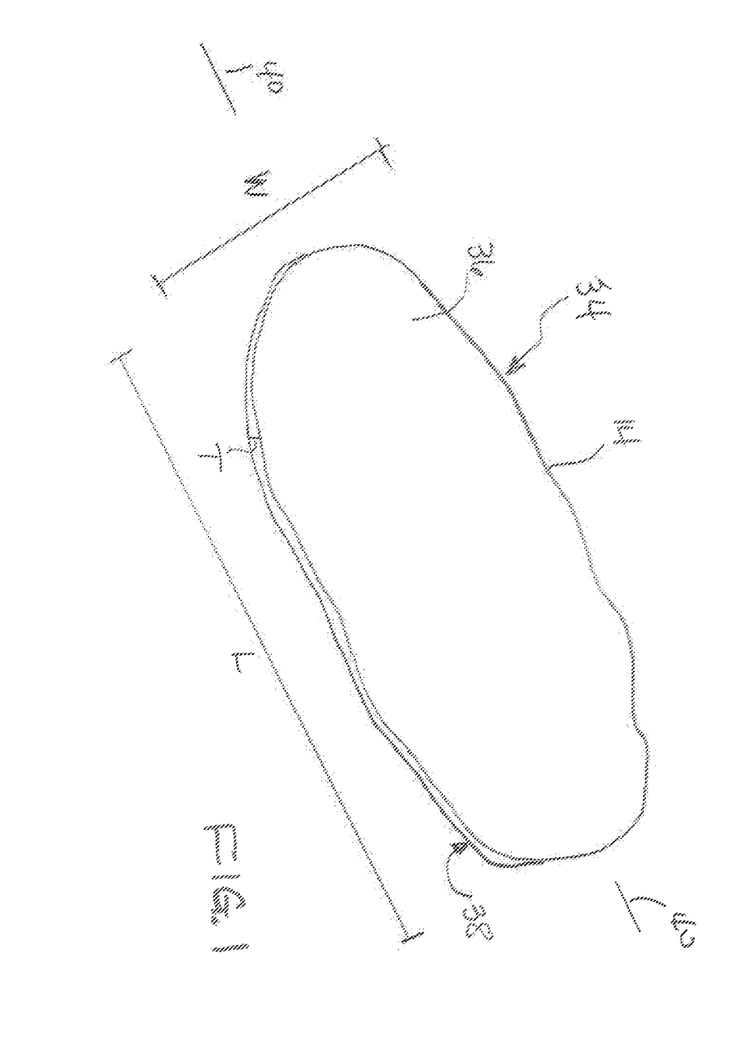
FIG. 1 is a perspective view of a first layer of the pet chew of the present disclosure.

The formation of the pet chew 10 is more specifically depicted in FIGS. 1-5. As shown in FIG. 1, the first layer 14 comprises a first slice 34 that is made from sweet potato. Sweet potato (*Ipomoea batatas*) is found in many varieties, at least sixteen of which are grown in the United States. The varieties come in a variety of colors, including orange, tan, yellow-orange, red and purple. Any variety of sweet potato may be used in the formation of the pet chew in accordance with the disclosure. Purple varieties of sweet potato, for example, may be particularly suitable for use.

A whole sweet potato is first cleaned of surface matter by washing. The sweet potato is preferably not peeled to maintain structural rigidity of the subsequently made slices, but may be peeled in some embodiments. The pointed ends of the sweet potato may be trimmed from the whole sweet potato before being sliced or the pointed ends may be unaltered. The washed sweet potato is then sliced along its length to produce slices that have a thickness T of generally about 1/16 inch. By "generally" is meant that the thickness of the slice can vary between 1 mm and 3 mm. The slices may be further washed to remove any surface material or may be processed further without washing.

While the formation of the sweet potato slices are described herein as being formed by cutting the sweet potato through its length, the sweet potato may alternatively be sliced through its thickness, or perpendicular to the longitudinal length of the sweet potato, to produce slices in accordance with the disclosure.

The first slice 34, or outer layer 14, has a first surface, or inner surface 36, and an opposing surface, or outer surface 38, which is oriented away from the first surface 36. The first slice 34 has a length dimension L and a width dimension W, which are dictated by the size of the whole sweet potato from which the slice was taken. By way of example only, the length dimension L of the slices may be from about four inches to about eight inches, and may be shorter or longer. By way of example only, the width of the slices may be from between three inches and four inches, but may be of wider or narrower width. Each slice of sweet potato may have a longitudinal axis 40.

A second slice 44 or inner layer 20, as shown in FIGS. 2A-2D, is formed in the same manner as described with respect to formation of the first slice 34 or outer layer 14 by taking slices from a whole sweet potato, the second slice 44 having a thickness of generally about 1/16 inch (between 1 mm and 2 mm). The second slice 44 or inner layer 20 also has a length dimension L2 and width dimension W2 which may be equivalent to the length dimension L and width dimension W of the first slice 34, or the length dimension L2 and width dimension W2 may be smaller.

Figure 2A:
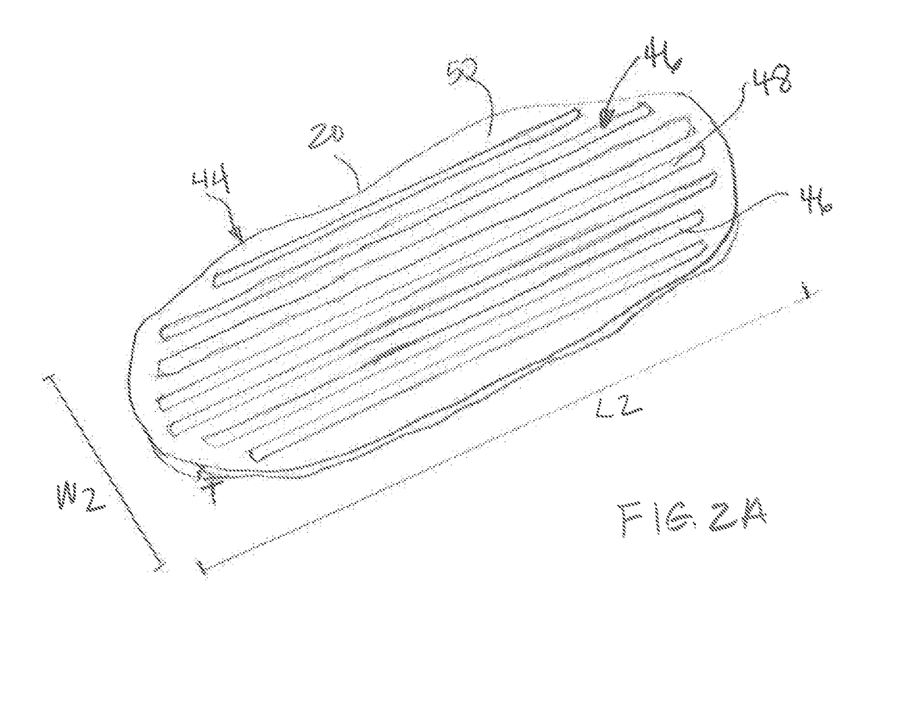
FIGS. 2A-2D are perspective views of exemplar embodiments of a second layer of the pet chew of the present disclosure, illustrating varying surface irregularities.
Figures 2B, 2C, 2D:
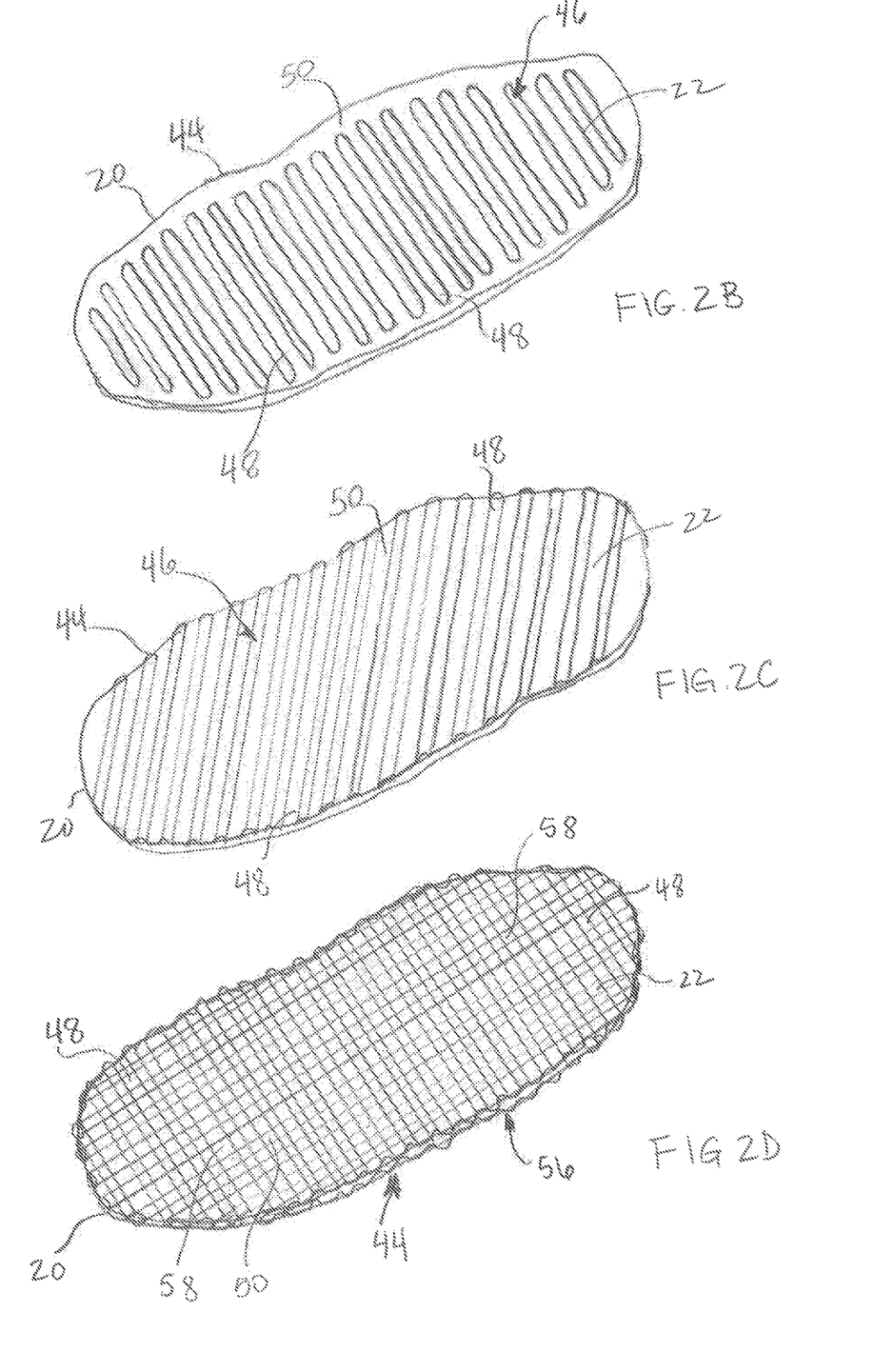

As depicted in FIGS. 2A-2D, the second slice 44 or inner layer 20 is further processed to provide at least one surface having irregularities 26. Surface irregularities 26 may be produced by further processing the second slice 44 with a configured slicing element, typically made of metal, to produce waves or ridges 48 in one or both surfaces of the second slice 44. In the embodiment shown in FIG. 2A, a first surface 50 of the second slice 44 is formed with ridges 48 which extend the length of the first surface 50. As depicted in FIG. 2B, the irregularities 26 may comprise ridges 52 formed on the first surface 50 across the width of the second slice 44. As depicted in FIG. 2C, the irregularities 26 may comprise ridges 48 formed on the first surface 50 of the second slice 44 at an angle to the length or width or the second slice 44.

In a particularly suitable embodiment, shown in FIG. 2D, the second slice 44 or outer layer 20, is processed with a slicing element that produces ridges 48 that are oriented along both the length and the width of the second slice 44 to produce a "waffle" pattern in at least one surface 50 of the second slice 44. The effect of the processing may be to produce irregularities on both a first surface 50 of the second slice 44 and on a second surface 56, which is oriented in opposite to the first surface 50 of the second slice 44. The "waffle" pattern produced by the slicing process may also produce a plurality of perforations 58 through the thickness T2 of the second slice 44. As with the processing of the first slice 34, the second slice 44, after being processed to form irregularities 26 in at least one surface thereof, may be washed to remove any unwanted surface debris, or may be used in the making of the pet chew 10 without further washing.

Figure 3:
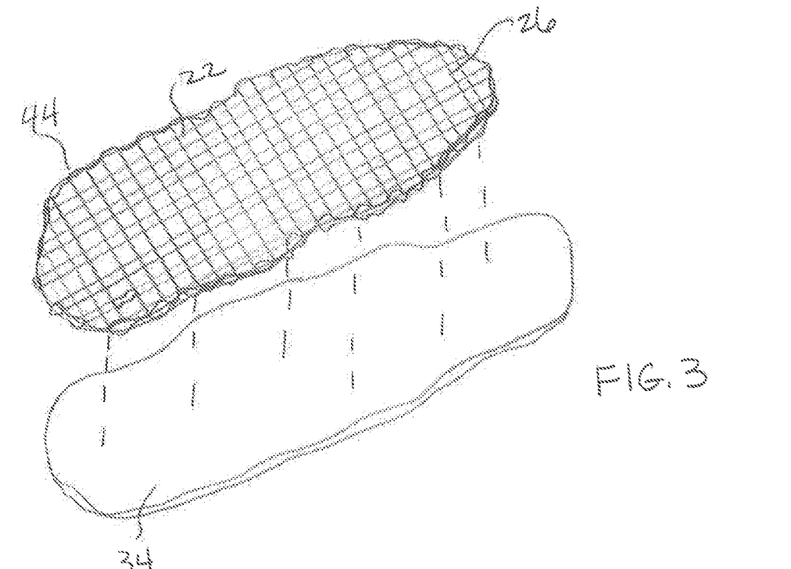
FIG. 3 is an exploded view in perspective of a first layer and second layer of the pet chew at initiation of formation of the pet chew.
Figure 4:
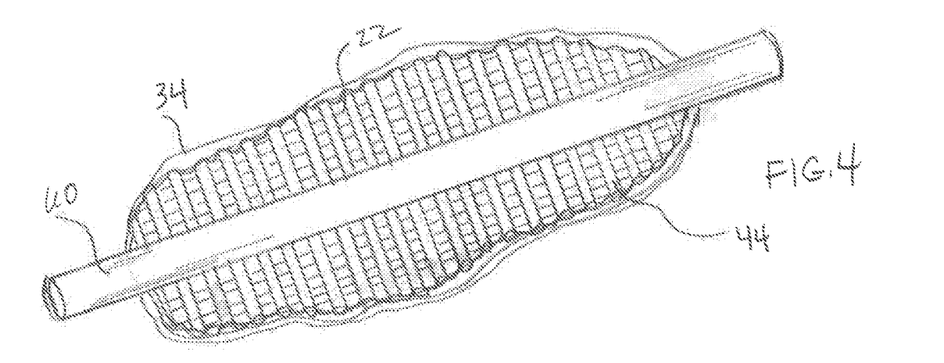
FIG. 4 is a perspective view of the dual layers of the structure with a mandrel positioned thereon.

FIG. 3 depicts the initial steps of forming the pet chew 10 in accordance with the disclosure where a second slice 44 is positioned adjacent a first slice 34 so that first slice 34 and second slice 44 are aligned about their respective perimeters and are in contact with each other, as seen in FIG. 4. As shown in FIG. 4, when the first slice 34 and second slice 44 are suitably aligned, a mandrel 60 is positioned adjacent the first surface 50, or inner surface 22, of the second slice 44 so that the irregularities 26 of that inner surface 22 are oriented away from the first slice 34, or outer layer 14, and toward the mandrel 60.

Figure 5:
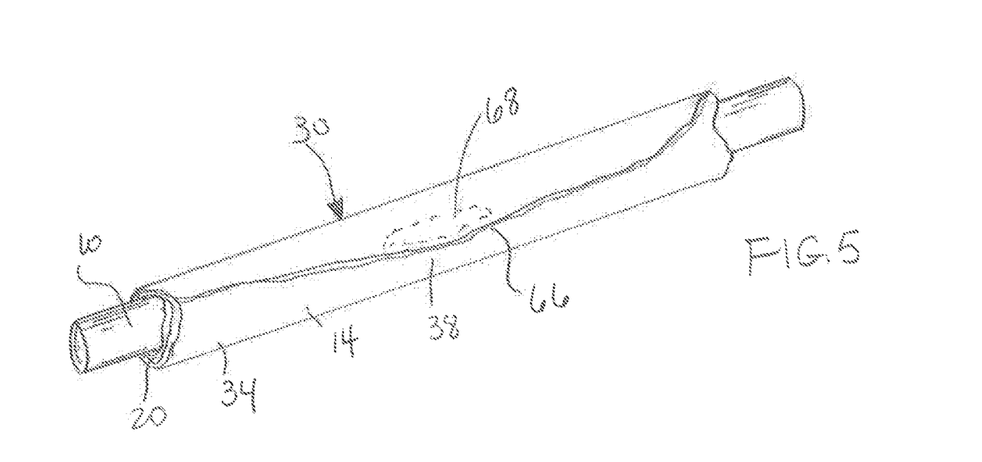
FIG. 5 is a perspective view of the tubular body in accordance with the disclosure formed about a mandrel.

The combination of first slice 34 and second slice 44 are then rolled about the mandrel 60 to form an elongated tubular body 30, as shown in FIG. 5. A free edge 66 of the first slice 34, or outer layer 14, and inner layer 20 is located along a short side of the first slice 34 and second slice 44 resulting from the rolling of the slices about the mandrel 60. The free edge 66 may be left unsecured to the outer surface 38 of the outer layer 14, as long as the tubular body 30 stays together in a tubular configuration. Alternatively, the free edge 66 may be secured to the outer surface 38 of the first slice 34 or outer layer 14 by application of a comestible adhesive 68, shown in phantom in FIG. 5, which provides a layer of comestible adhesive between an inner surface of the free edge 66 and the outer surface 38 of the first slice 34 or outer layer 14. Still alternatively, a mechanical device may be used to keep the tubular body 30 in a rolled configuration, such as a strap or tie that encircles the circumference of the tubular body 30.

The mandrel 66 may be sized in diameter from between 0.5 inch to one inch (1.25 cm to 2.5 cm). A particularly suitable diameter is between 0.5 inch and 0.75 inch. The combination of the first slice 34 and second slice 44 may be rolled about the mandrel 66 to form a tubular body 30 having two open ends 70, 72, which result when the mandrel 66 is removed from the tubular body 30 after processing (described further below). Alternatively, the edges 74 at one of the shorter ends of the two slices may be folded inwardly on the mandrel 66 to produce a closed end 76 of the tubular body 30.

The tubular body 30 is then treated with an application of heat to dehydrate the tubular body 30. In a particularly suitable embodiment, the tubular body 30 is treated with heat while the mandrel 66 remains in place within the tubular body 30 to assure that the tubular body 30 retains its shape. Alternatively, the mandrel 66 may be removed from the tubular body 30 before the application of heat. In another alternative method, the tubular body 30 may formed by rolling, as described, an then placed within a cylindrical form to maintain the tubular shape of the tubular body 30 while being heated.

The tubular body 30 is treated with heat that ranges from between 150° F. and 190° F. A particularly suitable heat may range from 155° F. to 160° F. The tubular body 30 is processed with the application of heat for a period of between nine hours and twelve hours, depending upon the initial water content of the sweet potato slices making up the tubular body 30. Generally, a processing time of eleven hours achieves the desired level of dehydration. The heating process should not exceed more than twelve hours because the nutritional value of the sweet potato slices may be degraded.

In an alternative method step, the tubular body 30 may be heated using an air frying process at a temperature of between about 150° F. to 195° F. for a period of between ten minutes and sixty minutes, depending on the amount of moisture in the tubular body 30. A particularly suitable treatment time may be between twenty minutes and thirty-five minutes. This process allows for a flash heating and dehydration processing that maintains a desirable moisture content of the finished product and maintains the nutritional benefits of the sweet potato.

Figure 8:
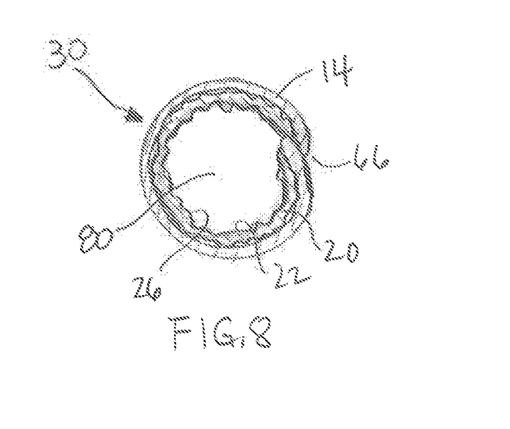
FIG. 8 is a view in cross section of the tubular body of FIG. 6, taken at line 8-8.

Following the heating process, the tubular body 30 is allowed to cool for approximately one to three hours. The mandrel 66 is then removed from the tubular body 30. The resulting dehydrated and cooled construct provides a tubular body 30 with an interior cavity 80, as shown in FIG. 8. The inner surface 22 of the tubular body 30 provides the interior cavity 80 with irregularities 26.

The resulting tubular body 30 that has been heated and cooled to become a dehydrated form has a moisture content that is ten percent or less. In a particularly suitable embodiment, the moisture content of the tubular body is between two and three percent. However, the moisture content may be from four percent to five percent; or the moisture content may be from three percent to six percent; or the moisture content may be from two percent to seven percent; or the moisture content may be from four percent to eight percent; or the moisture content may be from five percent to ten percent. The low moisture content allows for extended shelf-life and reduces the chance of formation of mold or bacteria on the tubular body 30, especially when sealed in air-tight packaging or container.

The irregularities 26 that are formed on the inside of the tubular body 30 provide an abrasive surface that cleans the teeth and gums of the animal as the tubular body 30 is chewed by the animal. While the first slice 34, or outer layer 14, of the tubular body 30 may, more typically, have a smooth outer surface 38, the outer surface 38 of first slice 34 may, alternatively, be processed to provide irregularities 82 on the outer surface 38, as depicted in FIG. 7, to increase the abrasive character of tubular body 30 for cleaning the animal's teeth.

In an alternative embodiment, a pet chew in accordance with the disclosure is formed from a single slice of sweet potato, in the manner previously described, which provides a first side of the slice that is relatively smooth or untextured. The opposing side of the slice defines a second side that is formed with irregularities in any of the manners previously described hereinabove, and as depicted in FIGS. 2A-2D. In this embodiment, the second side having the irregularities formed thereon or therein is oriented to define an inner surface of the pet chew when the single slice of sweet potato is formed into a tubular body as previously described. The tubular body thus formed may be processed under the same conditions as previously described with respect to dehydration and cooling of the tubular body.

Figure 9:
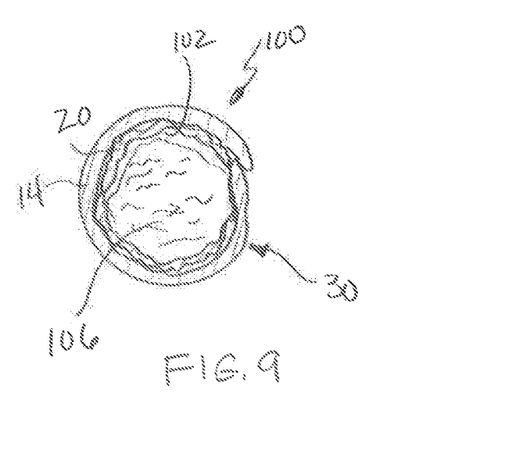
FIG. 9 is a view in cross section of a further aspect of the disclosure showing a pet chew with a viscous material positioned in the interior of the tubular body.

In a further aspect of the disclosure, a pet chew 100, shown in FIG. 9, may be formed in the manner previously described with respect to forming the dehydrated tubular body 30, and the interior cavity 80 of the tubular body 30 provides a space 102 into which a beneficial material 106 of suitable viscosity can be inserted to provide additional benefits to the animal as the animal chews on the pet chew 100. The dehydrated tubular body of the disclosure thereby provides the vehicle for delivery of the beneficial material. For example, the beneficial material 106 may be a viscous material made of natural ingredients that reduce plaque formation on the animal's teeth as a result of contacting the animal's teeth as the animal chews on the tubular body 30. Exemplar formulas of a beneficial material 106 that is formulated to reduce plaque on an animal's teeth are as follows:

Example I

A beneficial material for providing plaque reduction in dogs comprises:

| | |
|---|---|
| Water | 38% to 50% by volume |
| Sorbitol | 22% to 32% by volume |
| Sodium Bicarbonate | 0.01% to 7% by volume |
| Glycerin | 10% to 30% by volume |
| Potassium Sorbate | 0.2% to 0.4% by volume |
| Xanthan gum | 1.0% to 4.0% by volume |
| Chlorophyll | 0.015% to 0.5% by volume |
| Cinnamon extract | 0.01% to 0.5% by volume |
| Clove extract | 0.01% to 0.5% by volume |
| Pomegranate (liquid) | 0.05% to 2.0% by volume |
| Blueberry | 0.05% to 1.0% by volume |
| Zinc gluconate | 0.05% to 0.5% by volume |
| Papain | 0.01% to 0.2% by volume |
| Flavor | 0.01% to 1.0% by volume |
| Yucca extract | 0.05% to 1.0% by volume |
| Ascorbic acid | 0.01% to 0.5% by volume |
| Riboflavin-5-phospate | 0.01% to 0.5% by volume |

The plaque-reducing material of Example I is made by adding the water (purified) to a clean, stainless steel vessel and heating the water to 50 degrees C. The potassium sorbate (substitutable with sodium benzolate) is added and the liquid mixed until the potassium sorbate is dissolved. The zinc gluconate is added and the water mixed until the zinc gluconate is dissolved. The sorbitol is then added and the liquid mixed to evenly disperse the sorbitol. The papain (or other enzyme such as bromelain), cinnamon extract, clove extract, riboflavin and yucca are added and the mixture stirred until all ingredients are even dispersed. The pomegranate, blueberry, chlorophyll and ascorbic acid, and any additional flavorings, are added and the liquid is stirred to evenly disperse the additions. The sodium bicarbonate (or calcium carbonate), if used, is then added and the admixture is stirred to keep the bicarbonate in suspension. In a separate vessel, the xanthan gum (or guar or locust gum) is dispersed in the glycerin and the admixture stirred until the gum is evenly dispersed. The glycerin mixture is then added to the liquid in the other vessel and is mixed until all ingredients are evenly dispersed and thick.

Example II

A beneficial material for providing plaque reduction in cats comprises:

| | |
|---|---|
| Water | 45% to 50% by volume |
| Sorbitol | 18% to 22% by volume |
| Sodium Bicarbonate | 0.01% to 7% by volume |
| Glycerin | 10% to 30% by volume |
| Potassium Sorbate | 0.1% to 0.4% by volume |
| Xanthan gum | 1.0% to 2.0% by volume |
| Natural Fish Flavor | 0.05% to 1.0% by volume |
| Tetrasodium pyrophosphate | 0.01% to 5.0% by volume |
| Chlorophyll | 0.015% to 0.5% by volume |
| Fish Oil | 0.01% to 0.5% by volume |
| Taurine | 0.01% to 0.5% by volume |
| Cinnamon extract | 0.01% to 0.5% by volume |
| Clove extract | 0.01% to 0.3% by volume |
| Pomegranate (liquid) | 0.05% to 2.0% by volume |
| Blueberry | 0.05% to 1.0% by volume |
| Zinc gluconate | 0.05% to 0.5% by volume |
| Papain | 0.01% to 0.2% by volume |
| Yucca extract | 0.05% to 0.5% by volume |
| Ascorbic acid | 0.01% to 0.5% by volume |
| Riboflavin-5-phospate | 0.01% to 0.3% by volume |

The plaque-reducing material of Example II is made by adding the water (purified) to a clean, stainless steel vessel and heating the water to 50 degrees C. The potassium sorbate (substitutable with sodium benzolate) is added and the liquid mixed until the potassium sorbate is dissolved.

The zinc gluconate is added and the water mixed until the zinc gluconate is dissolved. The sorbitol is then added and the liquid mixed to evenly disperse the sorbitol. The papain (or other enzyme such as bromelain), cinnamon extract, clove extract, riboflavin and yucca are added and the mixture stirred until all ingredients are even dispersed. The pomegranate, blueberry, chlorophyll, ascorbic acid, taurine, fish oil and fish flavoring are added and the liquid is stirred to evenly disperse the additions. The sodium bicarbonate (or calcium carbonate), if used, is then added and the admixture is stirred to keep the bicarbonate in suspension. The tetrasodium pyrophosphate is added and the mixture is stirred to keep the pyrophosphate in suspension. In a separate vessel, the xanthan gum (or guar or locust gum) is dispersed in the glycerin and the admixture stirred until the gum is evenly dispersed. The glycerin mixture is then added to the liquid in the other vessel and is mixed until all ingredients are evenly dispersed and thick.

The foregoing viscous materials may be inserted into the space 102 provided by the inner cavity 80 of the tubular body 30 using a syringe or similar device loaded with the viscous material. The amount of material inserted into the inner cavity of the tubular body will vary with the varying size and length of the tubular body; however, the recommended amount to be inserted into the inner cavity of a tubular body would be that amount that substantially fills the inner cavity from one end of the tubular body to the other end. A lesser amount of material may be inserted into the tubular body, however.

The materials noted in Examples I and II should be inserted into the dehydrated tubular body just before giving the pet chew to the animal. Notably, for larger animals (e.g., dogs weighing twenty-five pounds or greater), a pet chew may be administered which is comprised of a tubular body of a length between four inches to seven inches or greater and which contains between two to three ml of material. For smaller animals (e.g., animals weighing between eight pounds and twenty-five pounds), a pet chew of four to seven inches in length can be easily broken into two pieces comprising two portions of two to three inches in length, and the smaller portions can be filled with approximately two ml of material for administration to the smaller animal. For animals that are very small, such as those breeds designated as "toy breeds," which weight less than eight pounds, the tubular body may be approximately one inch to two inches in length and may be filled with up to one ml of material. Alternatively, a pet chew having length dimension of approximately one to three inches can be provided to any size dog, with larger dogs being given two pet chews per day while medium-sized and smaller dogs receive one pet chew per day.

Other viscous materials may be inserted into the dehydrated tubular body of the disclosure to provide other benefits to the animal, such as providing supplemental nutrients or to administer therapeutic or medicinal agents the palatability of which are enhanced by combining the agents in a pleasant tasting sweet potato chew.

Test data derived from trials performed on dogs reveal the efficacy of the dehydrated tubular body to remove tartar from an animal's teeth. Test data also reveals the efficacy of the dehydrated tubular body as a vehicle for delivering plaque-reducing material in the removal of tartar and the reduction of plaque on an animal's teeth, as described further below.

Trials were performed on groups of fifteen dogs per trial. Two trials were performed on small to medium sized dogs (8-25 lbs.); one trial was performed on large dogs (25 lbs. or larger); and one trial was performed on toy dogs (8 lbs. or less). In each size group, fifteen animals were designated as control animals and were not allowed to consume anything other than dry food; fifteen animals were designated as a positive control group and were fed dry food as well as being provided with one dehydrated tubular body in accordance with the disclosure, the tubular body being filled with a placebo gel; and fifteen animals designated as the test group were provided with dry food and one dehydrated tubular body containing a plaque-reducing gel in accordance with the disclosure.

Preceding each trial, the teeth of the animals were scaled and polished to clean the teeth of calculus, or tartar, and plaque. The animal's teeth were examined to assure that all teeth were present and intact and that there was no evidence of severe periodontal disease or gingival inflammation. The trials were conducted for a period of twenty-eight days during which the animals were all feed the same dry food in the same quantities per day and were administered a pet chew in accordance with the disclosure, or were provided no pet chews as dictated by the designation of the test group in which the animal was placed. At the end of the twenty-eight day period, the animals were examined by licensed veterinarians and the teeth of the animals were scored by an established standardized scale, giving the condition of the teeth a score of between zero and three, where 0=no observable calculus (tartar); 1=scattered calculus covering less than one third of the buccal tooth surface; 2=calculus covering between one and two thirds of the buccal tooth surface with minimal subgingival deposition; and 3=calculus covering greater than two thirds of the buccal tooth surface and extending subgingivally. The results of the trials are set forth in the following table:

|  | Trial 1 - Small-medium dogs | | Trial 2 - Small-medium dogs | | Trial 3 - Large dogs | | Trial 4 - Toy dogs | |
| --- | --- | --- | --- | --- | --- | --- | --- | --- |
|  | % Reduction | Statistical analysis p-value | % Reduction | Statistical analysis p-value | % Reduction | Statistical analysis p-value | % Reduction | Statistical analysis p-value |
| Plaque, test vs negative control | 70.0% | <.00001 | 72.8% | <.00001 | 72.7% | <.00001 | 71.3% | <.00001 |
| Plaque, test vs positive control | 60.8% | <.00001 | 64.4% | <.00001 | 57.6% | <.00015 | 62.0% | <.00001 |
| Plaque, positive vs negative control | 23.5% | .00016 | 23.7% | .01645 | 35.6% | .00005 | 24.3% | .00346 |
| Calculus, test vs negative control | 74.8% | <.00001 | 75.6% | <.00001 | 75.6% | <.00001 | 75.2% | <.00001 |

-continued

|  | Trial 1 - Small-medium dogs | | Trial 2 - Small-medium dogs | | Trial 3 - Large dogs | | Trial 4 - Toy dogs | |
| --- | --- | --- | --- | --- | --- | --- | --- | --- |
|  | % Reduction | Statistical analysis p-value | % Reduction | Statistical analysis p-value | % Reduction | Statistical analysis p-value | % Reduction | Statistical analysis p-value |
| Calculus, test vs positive control | 55.1% | <.00001 | 53.2% | .00019 | 60.4% | .00007 | 59.7% | <.00001 |
| Calculus, positive vs negative control | 43.9% | .00004 | 47.9% | <.00001 | 38.5% | <.00006 | 38.5% | <.00002 |
| Gingivitis, test vs negative control | 363% | <.00001 | 227.3% | <.00001 | 437.5% | <.00001 | 386.7% | <.00001 |
| Gingivitis, test vs positive control | 47.3% | .00005 | 80.0% | <.00001 | 59.3% | .00010 | 92.1% | <.00001 |
| Gingivitis, positive vs negative control | 143.8% | .00084 | 81.8% | .00319 | 237.5% | <.00001 | 153.3% | .00049 |

The test data showed that those animals that were given the therapeutically-filled pet chew of the disclosure (test group) experienced at least a 53% reduction in calculus formation following the trial period, and at least a 58% reduction in plaque formation as compared to those animals that were given the dehydrated tubular body of the disclosure containing a placebo gel (positive control). The test group experienced at least a 75% reduction in calculus and at least a 70% reduction in plaque as compared to those animals that were not given the pet chews of the disclosure (negative control). The test data also demonstrated a two to four fold reduction in the occurrence of gingivitis following the trials.

The tests also demonstrated that those animals that were administered just the dehydrated tubular body containing placebo gel (positive control) experienced at least a 39% reduction in calculus and at least a 24% reduction in plaque as compared to those animals that were not given the pet chews of the disclosure (negative control).

Figure 10:
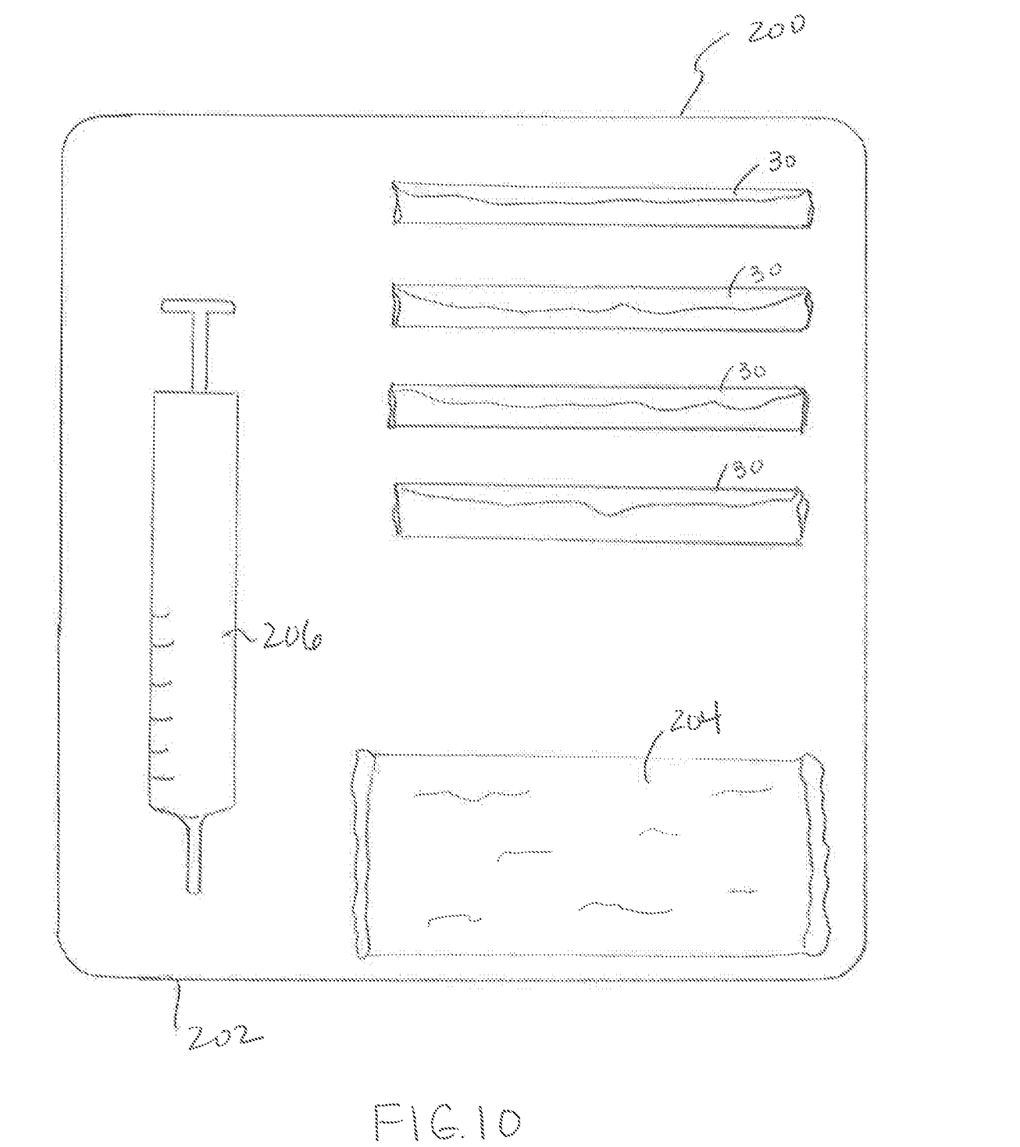
FIG. 10 is a depiction of a kit comprising a tubular body and a quantum of material for delivery to the interior of the tubular body in accordance with a further aspect of the disclosure.

In a further aspect of the disclosure, as depicted in FIG. 10, a kit 200 may be provided which contains one or more dehydrated tubular bodies 30 in an outer packaging unit 202. A quantum of beneficial material, contained in a separate sealed packet 204, is also included in the kit 200. The packet 204 may, preferably, be resealable and air-tight. The kit 200 may further include one or more syringes 206 for filling from the sealed packet 204 containing the beneficial material. Alternatively, the syringe(s) 206 may be pre-loaded with the beneficial material.

The pet chews 10, 100 of the disclosure are gluten free, sugar free, wheat free and contain no, or reduced, fat and are low in calories. The pet chews 10, 100 contain no artificial agents. The pet chews 10, 100 are naturally sweet and pleasant tasting to the animal, and are fully edible. Due to the special construction of the pet chews 10, 100, the sweet potato is fully digestible by the animal and will not cause intestinal blockages or produce toxic effects in the animal.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In addition, the foregoing describes only some embodiments of the inventions, and alterations, modifications, additions and/or changes can be made thereto without departing from the scope and spirit of the disclosed embodiments, the embodiments being illustrative and not restrictive.

Furthermore, inventions have described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the inventions. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. An edible pet chew, comprising:
   an outer layer made of at least one slice of sweet potato; and
   an inner layer of sweet potato positioned adjacent the outer layer of sweet potato, the inner layer having a surface oriented away from the outer layer that is processed to provide the said surface that is oriented away from the outer layer with irregularities,
   wherein the outer layer and inner layer are formed together as a rolled tubular body that is dehydrated.

2. The edible pet chew of claim 1, wherein said outer layer further comprises a single layer of sweet potato taken from a whole potato and having a thickness that is generally one-sixteenth of an inch.

3. The edible pet chew of claim 2, wherein the inner layer is formed from a slice of sweet potato having a thickness at an outer edge of the slice of sweet potato that is generally one-sixteenth of an inch.

4. The edible pet chew of claim 1, wherein the irregularities of the surface of the inner layer include perforations through the inner layer.

5. The edible pet chew of claim 1, wherein the irregularities of the surface of the inner layer include ridge formations that extend along the length of the inner layer, along the width of the inner layer or both along the length and width of the inner layer.

6. The edible pet chew of claim 1, wherein said tubular body has at least one open end providing access to an interior cavity of the tubular body.

7. The edible pet chew of claim 1, wherein the dehydrated tubular body has a moisture content of 10% or less.

8. The edible pet chew of claim 1, further comprising a plaque-reducing material positioned in an interior cavity of the tubular body, the plaque-reducing material containing natural plant extracts providing surfactant-based plaque-reducing agents selected from the group comprising *yucca* extracts, cinnamon extracts and clove extracts, and/or combinations thereof.

9. A method of making a pet chew, comprising:
providing a first slice of sweet potato taken from a whole sweet potato;
providing a second slice of sweet potato taken from a whole sweet potato;
processing the second slice of sweet potato to form irregularities on at least one side of the second slice of sweet potato;
positioning the second slice of sweet potato adjacent to the first slice of sweet potato to orient the at least one surface of irregularities away from the first slice of sweet potato;
placing the two adjacently positioned slices of sweet potato about a mandrel, with the second slice of sweet potato positioned closest to the mandrel and with the side having irregularities positioned adjacent to the mandrel to form a tubular body made of the first slice and second slice;
exposing the tubular body to a temperature of between 150° F. and 190° F. for a period of between nine hours and eleven hours; and
allowing the tubular body to cool for an additional one to three hours.

10. The method of claim 9, wherein the tubular body is exposed to elevated temperature while remaining positioned about the mandrel and is cooled for a period of between one and three hours while positioned about the mandrel, then followed by removal of the mandrel from the tubular body.

11. The method of claim 9, wherein a free end of the tubular body, resulting from the positioning of the first slice and second slice about the mandrel, is secured in place to maintain the tubular body in place about the mandrel for treating with an elevated temperature.

12. The method of claim 11, wherein the free end of the tubular body is secured in position by placement of comestible adhesive between the free end and the outer surface of the first slice of sweet potato.

13. The method of claim 11, wherein the free end of the tubular body is secured in place by wrapping a mechanical device about the circumference of the tubular body, the mechanical device being removed after the tubular body is treated with heat.

14. The method of claim 9, wherein the first slice of sweet potato is formed with a thickness dimension of generally one sixteenth of an inch, and wherein the second slice of sweet potato is formed with a thickness dimension of generally one sixteenth of an inch.

15. The method of claim 9, wherein the tubular body, following the heating and cooling steps, has a moisture content of between two percent and ten percent.

16. The method of claim 9, wherein one side of the first slice of sweet potato is formed with irregularities, which side is positioned about the mandrel to be oriented away from the mandrel and away from the second slice of sweet potato.

17. A method of making an edible pet chew, comprising:
providing a first slice of sweet potato;
providing a second slice of sweet potato and processing at least one side of the second slice of sweet potato to form irregularities on at least one side of the second slice of sweet potato;
positioning the second slice of sweet potato adjacent to the first slice of sweet potato to orient the at least one side of irregularities away from the first slice of sweet potato;
placing the two adjacently positioned slices of sweet potato about a mandrel, with the second slice of sweet potato positioned closest to the mandrel and with the side having irregularities positioned adjacent to the mandrel to form a tubular body of two layers of sweet potato;
exposing the tubular body to heat to dehydrate the tubular body; and
cooling the tubular body to form a dehydrated tubular body having a moisture content of between two percent and ten percent.

18. The method of claim 17, further comprising inserting into the interior or central cavity of the tubular body a material having therapeutic, nutritional and/or beneficial agents for the health of an animal.

\* \* \* \* \*